United States Patent
Webster et al.

(10) Patent No.: US 8,715,204 B2
(45) Date of Patent: May 6, 2014

(54) WIRELESS VAGINAL SENSOR PROBE

(75) Inventors: Wade W. Webster, Woodinville, WA (US); Richard S. Pollack, Boulder, CO (US)

(73) Assignee: Prima Temp, Inc., Boulder, CO (US)

( * ) Notice: Subject to any disclaimer, the term of this patent is extended or adjusted under 35 U.S.C. 154(b) by 221 days.

(21) Appl. No.: 13/182,565

(22) Filed: Jul. 14, 2011

(65) Prior Publication Data

US 2012/0016258 A1 Jan. 19, 2012

Related U.S. Application Data

(60) Provisional application No. 61/364,034, filed on Jul. 14, 2010.

(51) Int. Cl.
*A61B 10/00* (2006.01)
*A61B 5/00* (2006.01)

(52) U.S. Cl.
USPC .......................................... 600/551; 600/549

(58) Field of Classification Search
USPC .................................. 600/301, 549, 551, 591
See application file for complete search history.

(56) References Cited

U.S. PATENT DOCUMENTS

| | | | |
|---|---|---|---|
| 2009/0270948 A1* | 10/2009 | Nghiem et al. | 607/60 |
| 2009/0326410 A1* | 12/2009 | James et al. | 600/551 |
| 2010/0036208 A1* | 2/2010 | Koh et al. | 600/300 |
| 2010/0274105 A1* | 10/2010 | Rosenshein | 600/301 |

FOREIGN PATENT DOCUMENTS

DE 10345282 * 4/2005

OTHER PUBLICATIONS

Machine Translated version of DE 10345282. Machine translation was provided by espace.net on Dec. 17, 2013.*
Rodrigues, J. J. P. C. et al., A Novel Intra-body Sensor for Vaginal Temperature Monitoring, Sensors 2009, 9, 2797-2808; doi:10.3390/s90402797.

* cited by examiner

*Primary Examiner* — Brian Szmal
*Assistant Examiner* — Megan Leedy
(74) *Attorney, Agent, or Firm* — Santangelo Law Offices, P.C.

(57) ABSTRACT

Embodiments of the present invention are directed to a temperature sensing device that can comprise an elastic ring structure. The temperature sensing device can further comprise a transducer device, such as a temperature sensor, and a microprocessor, memory and wireless transmitter. Such an arrangement can incorporate a passive (battery free), battery assisted or active battery powered transponder circuit with temperature measurement capability. The elastic ring structure can be forced in a spring loaded state when elastically deformed thus becoming retained when disposed in a vaginal vault. In one embodiment, an active RF receiver or an RFID reader is brought in proximity to the temperature sensing and transmitting device arrangement, such as near a woman's pelvis from the outside to read the temperature and record it in a Central Processing Unit, CPU, associated with the receiver or RFID reader, such as a portable, handheld computer or wireless device.

19 Claims, 8 Drawing Sheets

WIRELESS VAGINAL SENSOR PROBE

CROSS-REFERENCES TO RELATED APPLICATIONS

The present application claims benefit under 35 USC 119(e) of U.S. Provisional Application No. 61/364,034, filed on Jul. 14, 2010 by Webster et al. and entitled "Wireless Vaginal Sensor Probe," of which the entire disclosure is incorporated herein by reference for all purposes.

BACKGROUND OF THE INVENTION

The present invention relates generally to using a probe device to measure temperature of vaginal vault that can be read wirelessly via a reader device.

A woman's body temperature changes during her period of ovulation. Close monitoring of her temperature can be used for ovulation detection to either achieve or avoid conception.

Today, a woman typically monitors and records her body basal temperature on a daily basis by way of inserting a thermometer into her vagina and recording her temperature. As a result of this complex daily procedure, a woman is more likely to forego recording her more accurate core temperature obtained vaginally and instead keep track of her oral temperature. Furthermore, although temperature monitoring has been used for years to help determine a fertile phase of a woman, the pattern recognition and relationship of temperature variation is not practically achieved due to the lack of frequent temperature monitoring and statistical analysis of baseline core body temperature. Other methods of obtaining a woman's body temperature over time include frequent temperature measured orally or from her axilla, however there are accuracy issues, and frequent insertion of a wired rectal probe or vaginal probe is inconvenient and uncomfortable. Hence there is a need for improved methods, systems, and apparatuses for obtaining an accurate basal temperature vaginally while reducing inconvenience and discomfort.

BRIEF SUMMARY OF THE INVENTION

Disclosed are embodiments of the present invention that include an elastic vaginal ring temperature sensing device that can comprise an elastic ring structure and incorporated wireless transmitting arrangement. The temperature sensing and transmission arrangement can further comprise a transducer device, such as a temperature sensor, and a microcontroller, memory and wireless transmitter. Such an arrangement can incorporate a passive (battery free), battery assisted or active battery powered Radio Frequency Identification (RFID) transponder circuit with temperature measurement capability. The temperature sensing and transmission device comprises an antenna portion and electronic portion (e.g., RFID integrated circuit and other components), linked to a temperature sensing portion that can sense the surrounding temperature. The elastic ring structure can be forced in a spring loaded state when elastically deformed thus becoming retained when disposed in a vaginal vault. In one embodiment, an active RF receiver or an RFID reader is brought in proximity to the temperature sensing and transmitting device arrangement, such as near a woman's pelvis from the outside to read the temperature and record it in a Central Processing Unit, CPU, associated with the receiver or RFID reader, such as a portable, handheld computer.

DETAILED DESCRIPTION OF THE INVENTION

Figure 1:
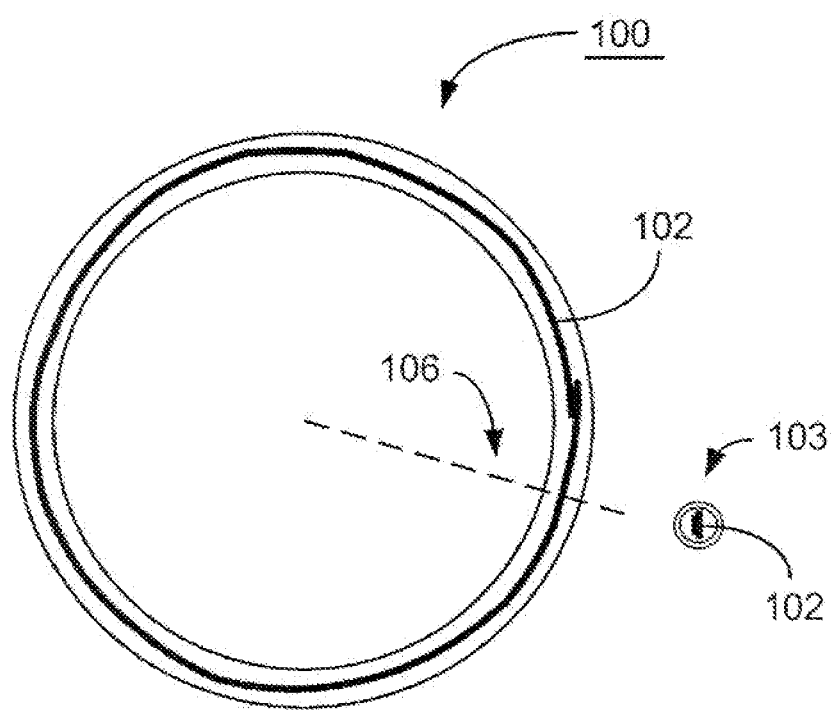
FIG. 1 is an illustration of an elastic vaginal ring with a temperature measurement and transmission arrangement according to an embodiment of the present invention.

In the following description, for the purposes of explanation, numerous specific details are set forth in order to provide a thorough understanding of various embodiments of the present invention. It will be apparent, however, to one skilled in the art that embodiments of the present invention may be practiced without some of these specific details. In other instances, well-known structures and devices are shown in block diagram form.

The ensuing description provides exemplary embodiments only, and is not intended to limit the scope, applicability, or configuration of the disclosure. Rather, the ensuing description of the exemplary embodiments will provide those skilled in the art with an enabling description for implementing an exemplary embodiment. It should be understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination can correspond to a return of the function to the calling function or the main function.

The term "machine-readable medium" includes, but is not limited to portable or fixed storage devices, optical storage devices, wireless channels and various other mediums capable of storing, containing or carrying instruction(s) and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

Referring to the drawings in general, and more specifically to FIG. 1, shown therein is an illustration of an embodiment of an elastic vaginal ring 100 with a temperature measurement and transmission arrangement comprised by a flexible circuit board arrangement 102 consistent with an embodiment of the present invention. A side view of the flexible circuit board arrangement 102 is shown coiled inside the elastic vaginal ring 100. Here, the vaginal ring 100 possesses a cross-section 103 that is circular and hollow or solid potted wherein the flexible circuit board arrangement 102 resides. In one embodiment, the flexible circuit board arrangement 102 can be approximately six inches long and 0.2 inches wide adapted to be accommodated by a two inch diameter vaginal ring 100. The flexible circuit board arrangement 102 can be an active temperature measurement and transmission device which is a miniature electronic circuit that generally can comprise for example an antenna, a radio transmitter, a small silicon-based microcontroller with memory, and a temperature measurement transducer.

Figure 2A:
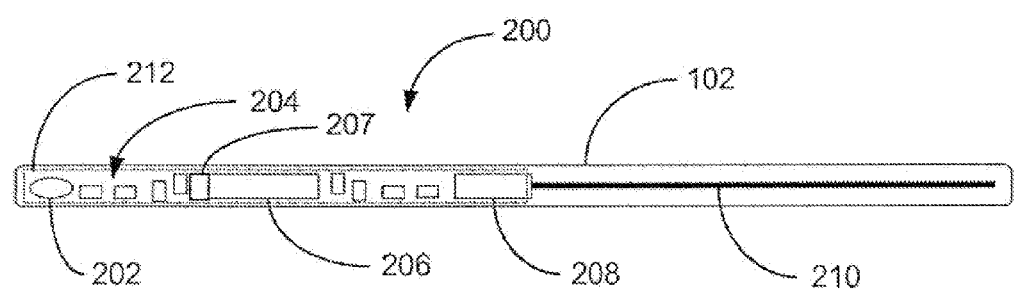
FIGS. 2A and 2B are diagrammatic illustrations of an active radio frequency transmission device according to one embodiment of the present invention.
Figure 2B:
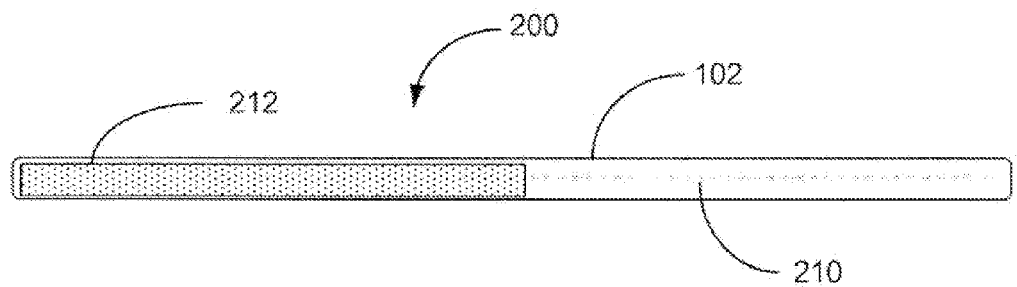

FIGS. 2A and 2B are diagrammatic illustrations of an active radio frequency device 200 consistent with embodiments of the present invention. FIG. 2A is a top view of the flexible circuit board arrangement 102, which supports the active transmitter assembly 200. As illustratively shown, the active transmitter assembly 200 generally can comprise a temperature transducer 202; conditioning circuitry 204 that can include a number of discrete components, such as capacitors, resistors, and diodes; a small silicon-based microcontroller 206 that interfaces with the temperature transducer 202; solid state memory 207; a radio transmitter 208; battery and voltage regulation circuits 212; and an antenna 210. FIG. 2B is a bottom view of the flexible circuit board arrangement 102 that more prominently displays the thin film battery 212.

The radio transmitter assembly 200 can be a type of electronic data generating and memory device, which can provide a means for measuring and providing information about the temperature sensed by the temperature transducer 202 (or other optional sensor input). The radio frequency device 200 can be considered an active device when, in certain embodiments, it possesses its own discrete power source, such as the battery 212. Such an active radio frequency device 200 can be programmed to periodically transmit recently measured temperature, periodically transmit several stored temperature readings or it can emit a signal containing its stored information whenever it enters and is queried by an RF field. In other embodiments, the radio transmitter assembly can be a passive radio frequency device. Unlike the active device described above, passive radio frequency transponder devices do not contain a power source (discussed in more detail in conjunction with FIG. 4). Rather, they generally operate in an RFID environment and are inductively or capacitively powered when they enter an RF field. Once powered, the passive and/or optionally semi-passive (battery assisted) transponder Integrated Circuit, IC, 400 can measure temperature of an integrated internal or external temperature transducer and emit a signal containing this measured information. Both active and passive radio frequency devices can include an analog circuit that detects and decodes data contained in the interrogating RF signal providing data to the active or passive radio frequency device 200 or 400. The microcontroller circuit in the active device and digital circuitry contained in the transponder IC in the passive device generally executes the data functions of the radio frequency temperature measurement and transmission device, such as measuring temperature, digitizing the data and causing the digital data to modulate the RF signal to transmit the measured data. In addition to retrieving and transmitting real-time measured data, both passive and active devices can permit new or additional information to be written to a portion of the radio frequency device's memory, and/or, optionally, can permit the device to manipulate data or perform some additional functions.

Embodiments of the active temperature sensing and transmitting device 202 can include a thermistor, Platinum Resistance Thermometer (PRT), other analog temperature sensor or, optionally, may be a temperature sensor with integrated digital circuitry that provides a digital output. Analogue temperature sensors can include a Temperature Conditioning Circuit (TCC) 204, which incorporates electronic components that provide for proper voltage and output levels for the Analog to Digital (A/D) input to the microcontroller 206. If the temperature sensor is a digital output device, it can be connected directly to the Serial Programming Interface (SPI) bus (not shown) or I2C bus (not shown) associated with the microcontroller 206. In several embodiments, the temperature sensor 202 may be calibrated or, optionally, may have inherent temperature measuring accuracy that facilitates an acceptable temperature accuracy, such as to a +/−0.1 degree Celsius accuracy, for example. Characteristics of the temperature sensor output function may be programmed into the memory 207 to improve accuracy.

Figure 3:
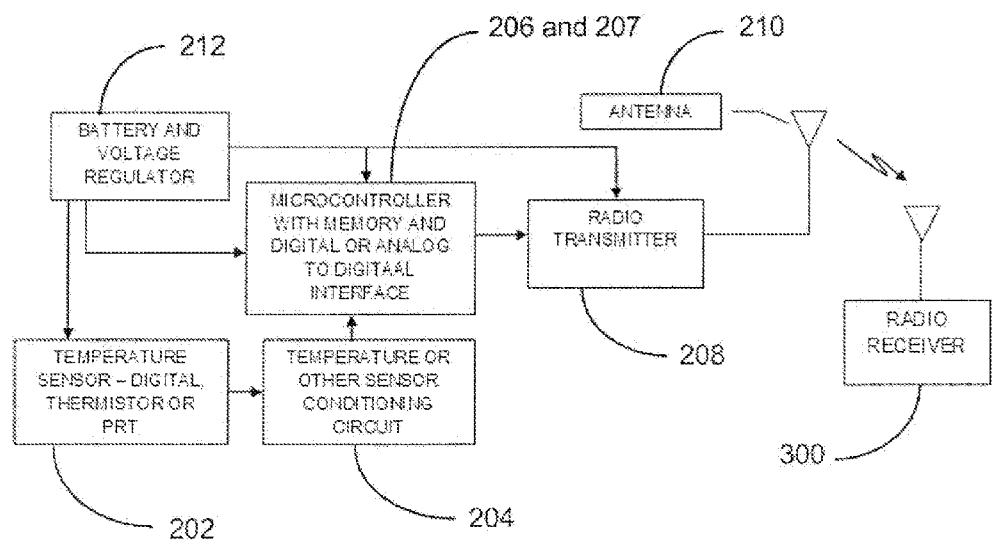
FIG. 3 is a block diagram of an active transmitter assembly 200 operable with a radio receiver according to one embodiment of the present invention.

FIG. 3 is a block diagram of an active transmitter assembly 200 operable with a radio receiver 300 consistent with embodiments of the present invention. In one embodiment, the microcontroller 206 can run a program that will cause it to periodically measure the output of the temperature sensor 202 and convert measurement data into digital units that can be stored in memory 207. These may be engineering units, such as degrees Celsius, or may just be digital bits that are converted into engineering units in the radio receiver 300, for example. The digital information from the temperature sensor 202 and other information such as time, date and indicia, such as an identification number, of the specific elastic vaginal ring 100 can be input to the radio transmitter 208 on periodic intervals, for example every 15 minutes, which can, in turn, be transmitted by the radio transmitter 208, via the Antenna 210, to a radio receiver 300.

The radio receiver 300 may operate at any authorized frequency, or optionally, be transmitted in the UHF band between 308 MHz and 434 MHz. This band has the advantages of longer transmission ranges than lower frequencies such as 13.56 MHz while penetrating the body better than higher frequencies, such as 900 MHz or 2.4 GHz. The 308 MHz to 434 MHz band is approved for use by the U.S. FCC and broadly by other countries without requiring a license for each unit. The reception distance of such a radio signal could exceed 10 feet.

A battery 212 together with voltage regulation circuitry can supply the proper voltage to each of the circuit elements. The battery 212 can, in one embodiment, be a thin film lithium ion or zinc-manganese dioxide chemistry battery that can be bent or curved.

In one embodiment, the radio receiver 300 may be a simple stationary device with power line or battery power that may display data for an extended period, e.g., 30 days or more, in graphical or tabular form, for example. The receiver 300 may be programmable to alert an end user based on a predetermined thresholds or trends. Alternately, the receiver 300 may be attached to a personal computer such that a program running on the personal computer could provide alerts, alarms, historical data and other information to the end user. Such an exemplary embodiment will be described in detail below with reference to FIG. 7.

The radio receiver 300 may, optionally, be a portable device carried by the end user. One form of a portable receiver 300 includes a receiver embedded into a custom Smart Phone case. The case can be designed so that the Smart Phone data port is connected to the receiver 300. Alternatively, the Smart Phone or other receiver 300 may receive data via Near Field Communication (NFC), WiFi, Bluetooth, or another type of receiver of the Smart Phone or portable device. The data gathered by the receiver 300 can potentially be manipulated by a Smart Phone application that would provide alerts or other information to the end user automatically or upon manual actuation.

Other embodiments of the radio transmitter 208 and receiver 300 may be employed. The radio transmitter 208 may also contain a radio receiver capability and the radio receiver 300 may also contain a transmitter. In this case, both would be transceivers. Here, the radio receiver 300 can transmit queries to radio transmitter 208 that can enable the transmitter 208 to transmit upon query as opposed or in addition to automatically transmitting on a fixed period. In this way, the data from the memory 207 and microcontroller 206 can be transmitted when it is range of the receiver 300. In addition, this can enable the receiver 300 to send an acknowledgement to the transmitter 208 that data was correctly received (for example after running error detection algorithms), and this can further ensure valid data is received, or could enable the receiver 300 to warn the end user that data was not received properly.

In one embodiment, the program running on the microcontroller 206 causes the data from each temperature measurement to be retained in memory 207, and possibly including the time associated with each measurement. When queried by a nearby receiver, the stored data is transmitted to the receiver. For example, 24 hours or more of data in the active transmitter assembly memory could be stored, and all or some of this data could be transmitted when the transmitter assembly is queried. In this way, the user only needs to interrogate the transmitting device periodically, e.g., once per day, to collect measured data. In this example, the oldest data can optionally be automatically erased from memory and only the most recent data retained. This illustrative example is one of many variations of managing, transmitting and collecting data.

Figure 4:
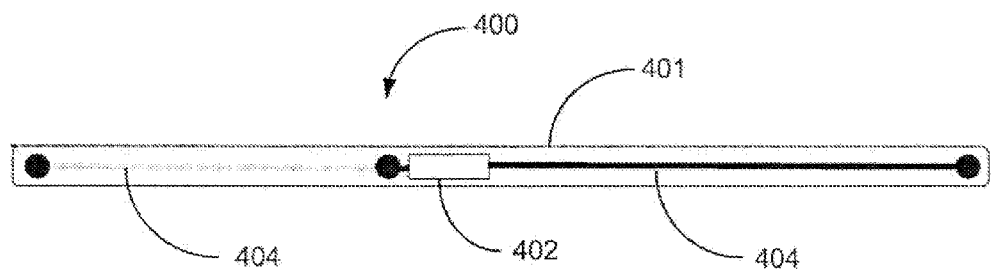
FIG. 4 is an illustration of a passive RFID transponder arrangement according to one embodiment of the present invention.

Another embodiment of the present invention employs a passive radio frequency transponder device, which in the forgoing embodiment can measure temperature with circuitry integrated into the IC circuit chip. Alternately, a temperature transducer element can be attached to external sensors via interfaces on the IC circuit chip. One example of a passive RFID transponder chip that has internal temperature measurement circuitry and external sensor interfaces is the MLX90129 IC manufactured by Melexis Microelectronic Integrated Systems N.V., Ieper, Belgium. FIG. 4 is a diagrammatic illustration of a passive radio frequency transponder assembly 400 consistent with an exemplary embodiment of the present invention. The flexible circuit board 401 supports the passive transponder assembly 400 that operates generally in an RFID environment. As illustratively shown, the passive transponder assembly 400 generally can comprise a transponder integrated circuit with temperature sensing 402 and a printed trace antenna coil 404 with vias. The transponder integrated circuit with temperature sensing 402 can incorporate circuitry to function as an RF powered sensing device that is operatively functional with the antenna 404. In one embodiment, the flexible circuit board 401 is approximately six inches long and 0.2 inches wide to be accommodated by a two inch diameter vaginal ring 100. Presently, RFID transponder chips that measure temperature are available in standardized Low Frequency (LF) (134.2 KHz), High Frequency (HF) (13.56 MHz) and Ultra High Frequency (UHF) (915 MHz) bands. In the embodiment of FIG. 4, if the assembly is an LF or HF embodiment, the antenna 404 can be a single or multi turn loop that would inductively couple with the magnetic field emanated by a radio receiver/reader device 300. A magnetic loop antenna can be created when Flexible Circuit Board 401 is curled into a ring such that the vias at the end of the antenna traces 404 overlap. The end vias can then be soldered, glued with conductive epoxy, or riveted together, creating an electrically continuous loop. If the assembly is a UHF embodiment, the antenna 404 can optionally be a dipole arranged to couple to the E-Field emanated by the radio receiver/reader device 300. In the illustrative embodiment of FIG. 4, the traces are not connected.

In one passive transponder embodiment, the radio receiver/reader device 300 can be a suitable RFID reader that can query the transponder 400 by sending a signal that energizes the transponder IC 402 causing it to measure temperature and transmit the temperature to the radio receiver/reader device 300. For example, the signal can comprise a Near Field Communications (NFC) signal according to NFC protocol standards ISO/IEC 18092/ECMA-340 or ISO/IEC 21481/ECMA-352.

In the present embodiment, the transmitter assembly 200 or 400 can be curled into ring and integrated by being encapsulated in an elastic polymer. In one embodiment, the elastic vaginal ring 100 encapsulates the transmitter assembly 200 in a hollow tube and in another embodiment, the elastic vaginal ring 100 encapsulates the transmitter assembly 200 in a solid encapsulant, that is, the elastic polymer is substantially intimately formed around the transmitter assembly 200. For example, the elastic polymer can comprise one of several silicones approved by the Food and Drug Administration (FDA) for use inside the human body. The cross-section of the ring 100 may be round or another shape. The shape of the ring 100 may be circular, elliptical, oval, facetted or semi-facetted in shape, just to name a few examples. As will be further discussed, the elastic vaginal ring 100 is intended to be inserted vaginally and its handling is similar to birth control rings, such as the NuvaRing of Merck and Company, Inc., headquartered in Whitehouse Station, N.J., for example.

Figure 5:
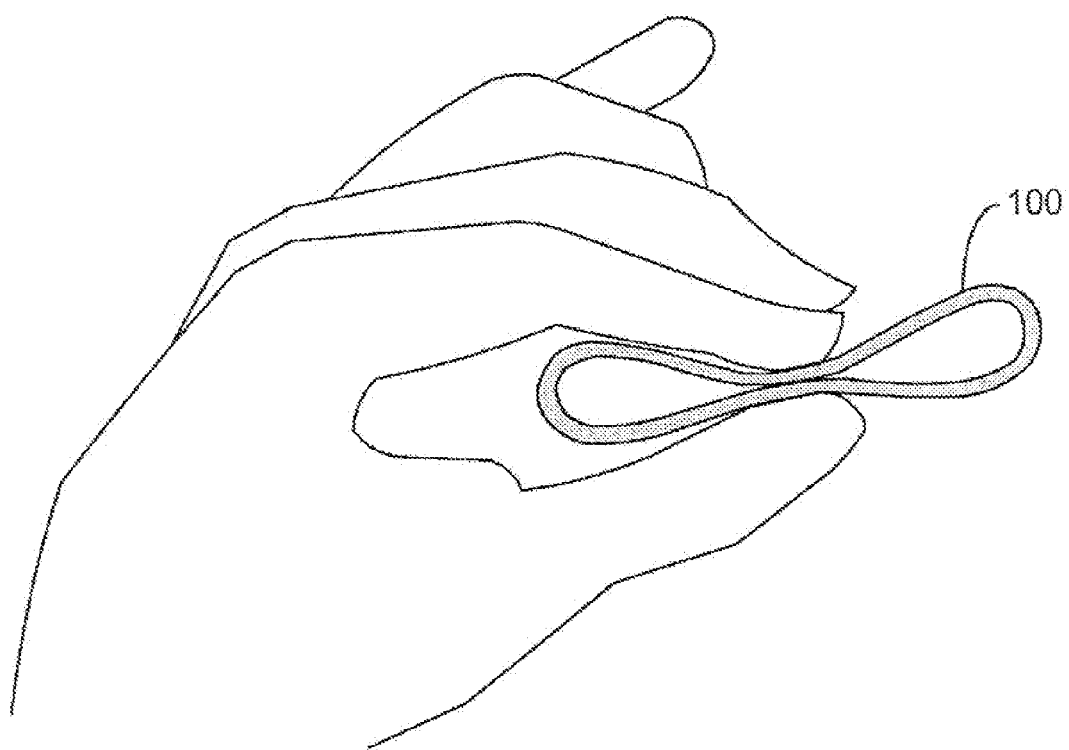
FIG. 5 is an illustration of a hand elastically deforming a vaginal ring according to one embodiment of the present invention.

FIG. 5 is an illustration of a human hand compressing the elastic vaginal ring 100 between a thumb and forefinger. As shown in FIG. 1, the elastic vaginal ring 100 can be an "O" shaped ring that is deformable when compressed as shown. The elastic vaginal ring 100 can be hollow containing a flexible RF circuit device, such as flexible circuit board arrangement 102, or optionally solid encapsulated around a transducer device 200 or 400, just to name two examples. The elastic vaginal ring 100 is ideally between 1 inch and 4 inches for a mature human woman. The elastic vaginal ring 100 can be in other dimensions depending on other applications deviating from a human woman vagina 600.

Figure 6:
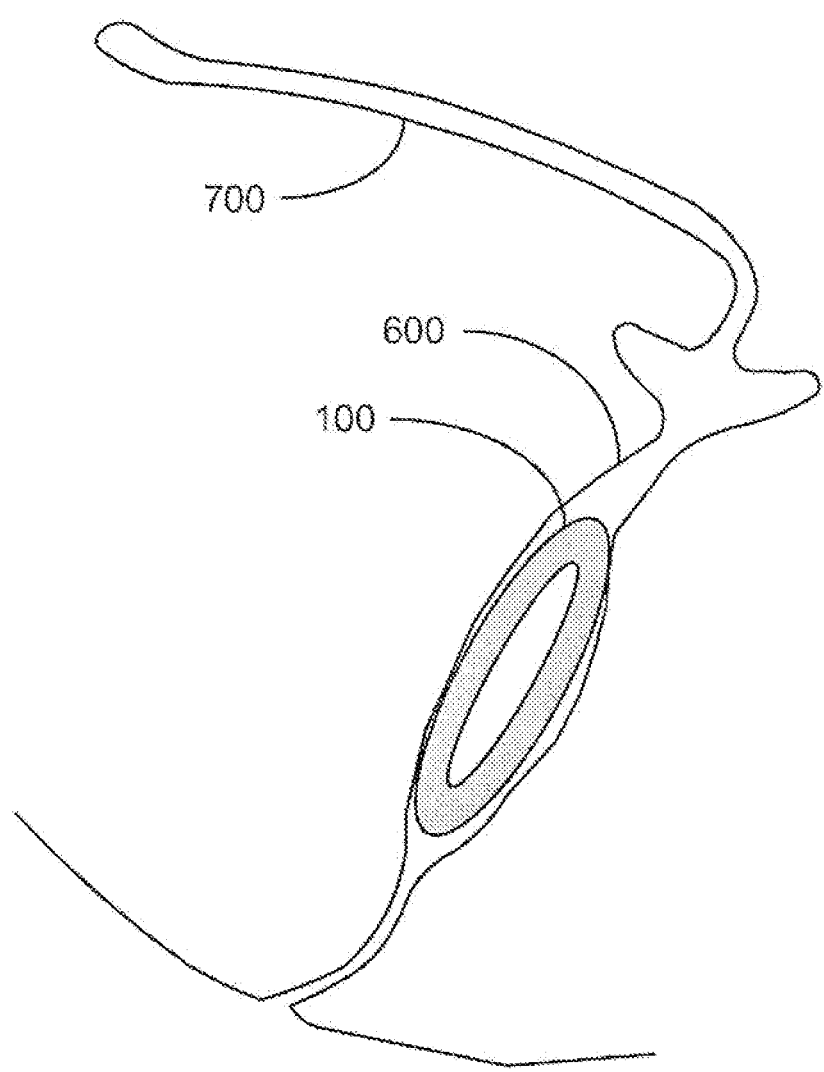
FIG. 6 is an illustration of an elastic vaginal ring disposed in a vaginal vault according to one embodiment of the present invention.

FIG. 6 is an illustration of the elastic vaginal ring 100 disposed in a vaginal vault 600 wherein the uterus 700 is shown for reference. Here, the elastic vaginal ring 100 is forced in a spring loaded state when elastically deformed thus becoming retained when disposed in the vaginal vault 600. The temperature measuring device, such as the temperature transducer 202 of FIG. 2, measures the vaginal temperature when disposed in the vaginal vault 600. Data generated via the active transmitter device can be received by a radio receiver/reader device 300 that is located in an environment that is external to the vaginal vault 600, such as near a woman's pelvis. Such as receiver device 300 can be hand-held, for example, or optionally can be integrated in a larger device or as a standalone unit. In such an active device embodiment, the communication can be two-way. The receiver device 300 can create a radio frequency signal received by a transceiver, such as may be combined with radio transmitter 208. When said signal is received, the microcontroller 204 can cause measurements to be taken via transducer device, such as the temperature device 202, processing the measurements and transmitting the measurements to the reader device 300. In a passive transponder embodiment, the reader/receiver device 300 can emanate enough energy to activate and power transponder IC 402, causing measurements to be taken via temperature circuitry integrated in transponder IC 402 and that can then be transmitted to reader/receiver device 300. Data obtained by the reader/receiver device 300 from the circuit board arrangement 202 or 402 can be manipulated by software executed in the reader/receiver 300, for example, as described below with reference to FIG. 9. Such data can be used to generate graphs or predictions to predict female fertility phases, early diagnosis of disease, or optimal times to take body samples for human diagnostic tests. In yet another optional embodiment, data acquired by the elastic vaginal ring 100 can have limited access to those with a key, or password. Optionally, the data acquired by the elastic vaginal ring 100 can be encrypted.

Embodiments of the elastic vaginal ring 100 can include chemicals that are released in a controlled manner when the elastic vaginal ring 100 is disposed in a vaginal vault 600. Optional transducers can also be employed such as a transducer that measures pH, salt concentrations, and mucus viscosity, for example. This can be accomplished by integrating multiple sensors in elastic vaginal ring 100. Optionally, multiple like sensors can be integrating in the elastic vaginal ring 100 to provide redundant measurements for comparison. The transducer/s can make measurements when in the presence of an RF field, or optionally, if the transducer device is active, such as the active radio frequency transducer device 200, measurements can be taken continuously or in intervals.

Further embodiments of the elastic vaginal ring 100 can include cross-sections that have shapes such as a circle, a polygon, an ellipse, a semicircle and substantially straight line, a semi-ellipse and substantially straight line, at least two semi-ellipses. The cross-section is defined by a single radial line 106 that extends from the center of the vaginal ring which passes through the cross-section, as illustratively shown in FIG. 1.

Further embodiments can include a method to use an elastic vaginal ring 100 as featured herein including: bending an elastic ringed shaped structure 100; inserting the elastic ringed shaped structure 100 in a vagina 600 wherein the elastic ringed shaped structure 100 is essentially retained in the vagina 600 via a spring-load effect from the bending; measuring temperature of the vagina 600 via a transducer arrangement, such as the transponder integrated circuit with temperature sensing 402, integrated with the elastic ringed shaped structure 100 after the inserting step; retaining data associated with the temperature in a memory device associated with the transducer arrangement; and transmitting the data to a reading device, such as the reader device 300, that is located outside of the vagina 100. Optionally, a second parameter can be measured, in some cases other than said temperature, via a second transducer integrated with said elastic ringed shaped structure 100 after said inserting step. Optionally, the method can further comprise energizing said transducer arrangement via an energy field created by said reading device. The method can further comprise transmitting said data from said transducer arrangement to said reading device when energized from said energy field. Electrical parameters generated by the sensor device, such as the temperature device 202, can be converted to a digital word, or words (data), that are transmitted to the reading device 300, which can be stored in memory in the reading device 300 for later transfer to a computing system where the data can undergo further analysis or manipulation, for example. Optionally, adding data logging circuitry to the IC memory device, such as the memory 207 of FIG. 2A, so that the temperature history can be logged and transferred to a reading device 300 wirelessly.

RFID integrated circuit chips are commercially manufactured by Phase IV Engineering, of Boulder, Colo., models EM4215, Melexis (MLX 90129) and IDS (SL13A_SD). These IC chips have internal temperature sensing and interface ports to add external sensors. These chips are deployable on circuit boards 402 as previously discussed.

Figure 7:
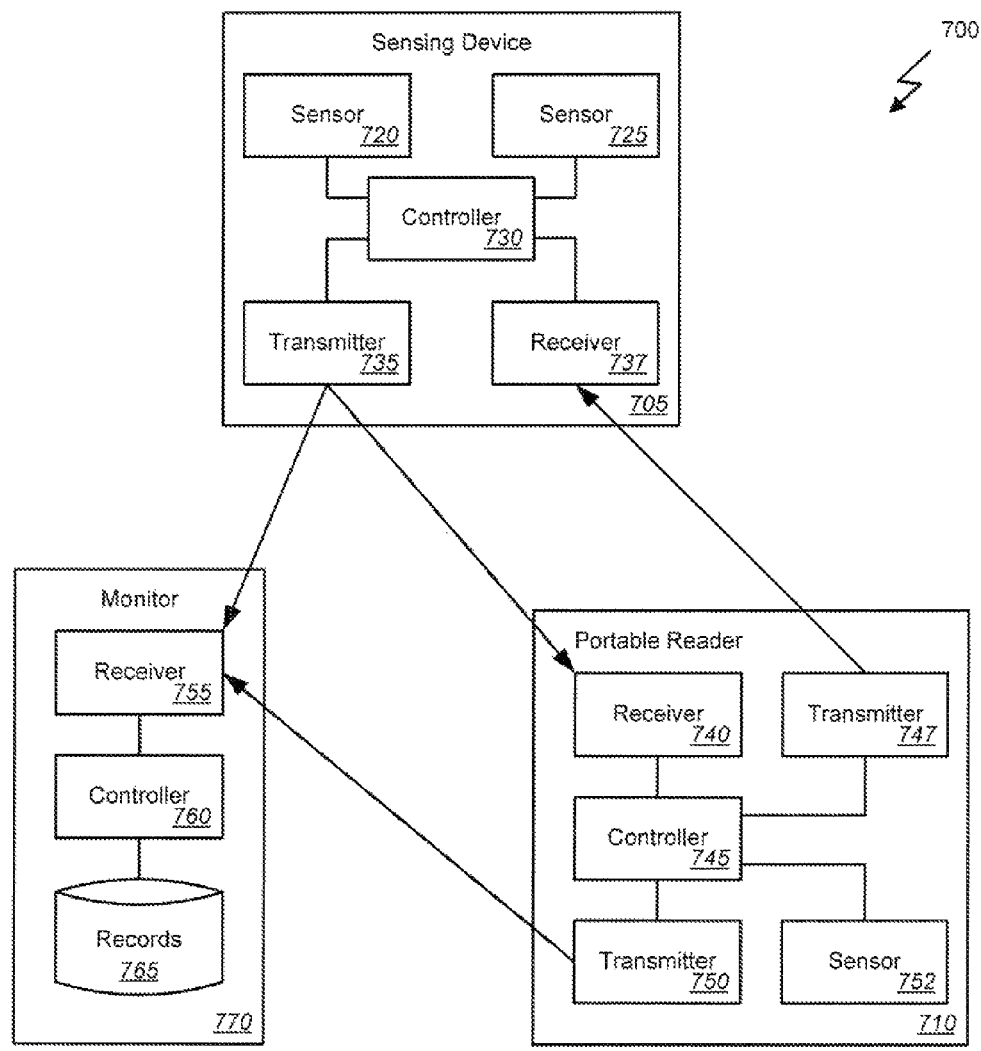
FIG. 7 is a block diagram illustrating components of an exemplary operating environment in which various embodiments of the present invention may be implemented.

FIG. 7 is a block diagram illustrating components of an exemplary operating environment in which various embodiments of the present invention may be implemented. This example illustrates a system 700 utilizing a sensing device 705 such as may be disposed in a vaginal ring as described herein and including two sensors 720 and 725. However, as noted above, the sensing device 705 need not include more than one sensor. Also as noted above, the sensors 720 and 725 can comprise temperature sensors or any of a number of other types of sensors depending upon the implementation of the system. Optionally, the sensing device 705 can include a receiver 737, such as RFID, near field or other RF receiver that enables the sensing device 705 to receive communication from a reader device 710. Also as noted above, the sensing device 705 itself can be incorporated in a small, thin, and flexible package, i.e., mounted on a flex circuit and utilizing an IC chip that integrates a microcontroller or other controller 730, a beacon radio and a RFID communication circuit 737 or other transmitter 735 into a single IC chip. In another implementation, the sensing device 705 can include a microcontroller or other controller 730, a beacon radio or other transmitter 735 in a single IC chip and a second ultra high frequency (UHF) RFID communication IC chip (not shown here) and having the UHF RFID communication IC share the same antenna as a UHF beacon radio. Such an implementation can include detection and switching circuitry (not shown here) to switch the antenna into the RFID IC chip during RFID function and into the beacon radio circuit during beacon mode.

Optionally, the system 700 utilizing sensing device 705 can include a system 770 in communication with the sensing device 705 and receiving and evaluating the temperature data from the sensing device 705. Such a system 770 can include a receiver 755, controller 760, and memory 765. This system 770, implemented in a personal computer, laptop, or other computing device as described below with reference to FIG. 8 may receive the temperature data from the sensing device(s) 705 through the receiver 755. The receiver 755 may communicate with the rest of the system 700 via hardwiring or via a variety of radio transmitter connections, including WiFi and Bluetooth connections. The controller 760 and this system 770 can execute an application for utilizing the received sensor data such as the processes described below with reference to FIG. 9. Based on these processes, the controller 760 may write records of the received sensor data to the memory 765 of the system over time and for a particular subject and provide notifications of detected changes from a baseline, e.g., a rise in core body temperature indicating a possible onset of ovulation.

Additionally or alternatively, the system can include a portable reader device 710. The reader device 710 may be implemented, for example in a Personal Digital Assistant (PDA), cell phone, or other portable computing device. The reader device 710 can include a receiver 740 such as a Bluetooth, RFID, NFC, or other RF for receiving sensor data transmitted from the sensor device 705 and a controller 745. Optionally, the reader device 710 may also include a transmitter 750 or other communication channel such as a Bluetooth, WiFi, or other RF for communicating with the monitor system 770 or other system or device. In other cases, the reader 710 may include a USB or other port through which sensor data collected by the reader device may be provided to the monitor system 770 or other system or device.

Optionally the reader device 710 may include transmitter 747 that communicates with the sensing device 705 via a Bluetooth, Near Field Communication (NFC), Radio Frequency Identification (RFID), or other connection. As noted above, this communication link permits the reader 710 to query the sensing device 705 to cause it to transmit data immediately, allowing real time reading of the sensor data, and further enables programming or turning on or off the sensing device 705.

According to one embodiment, the sensing device 705 can encrypt the temperature data prior to transmission to the system 715, local receiver device 712 or the reader 710. For example, the controller 730 of the sensing device 705 can use the AES standard to eliminate unauthorized decoding of data and enable conformance to privacy and confidentiality requirements.

A sensing device 705 as described herein, together with a supporting system 700 and/or reader 710 and/or monitoring system 770, can support a number of different communication modes. For example, a sensing device 705 and system 700 can support: 1) a beacon mode RF transmission, for example in the UHF frequency range, which transmits to a receiver, e.g., 10 feet or more away, at regular, programmable intervals, say once every five minutes; 2) transmits when a temperature change beyond a set threshold occurs (alarm). This threshold may be based on a change from each individual's baseline instead of a pre-established temperature. In some cases, a sensing device can include a proximity, RFID type communication link in addition to the beacon transmission. This RFID link enables a real-time inquiry function which can be achieved by adding a low frequency, high frequency or ultra-high frequency antenna and RFID read/write circuit 737 that is in communication with the sensing device controller 730. This link can permit, for example: a proximity real-time inquiry from a hand-held device (such as reader 710); and turning on the sensing device from a proximity handheld device to eliminate a switch for turning on the sensing device prior to being inserted. In some implementations, the sensing device 705 can log temperature readings and time/date into memory for later retrieval (data logger) via the real-time inquiry mode. This allows, for example, a record of the recent past to be evaluated. One embodiment can include a sensing device with an ultra low energy Bluetooth circuit that serves as the proximity inquiry link. This can allow proximity inquiry and programming to be done by a mobile device such as a smart phone equipped with Bluetooth functionality. Another option is that both the reader 710 proximity communication and the beacon function are via Bluetooth.

Figure 8:
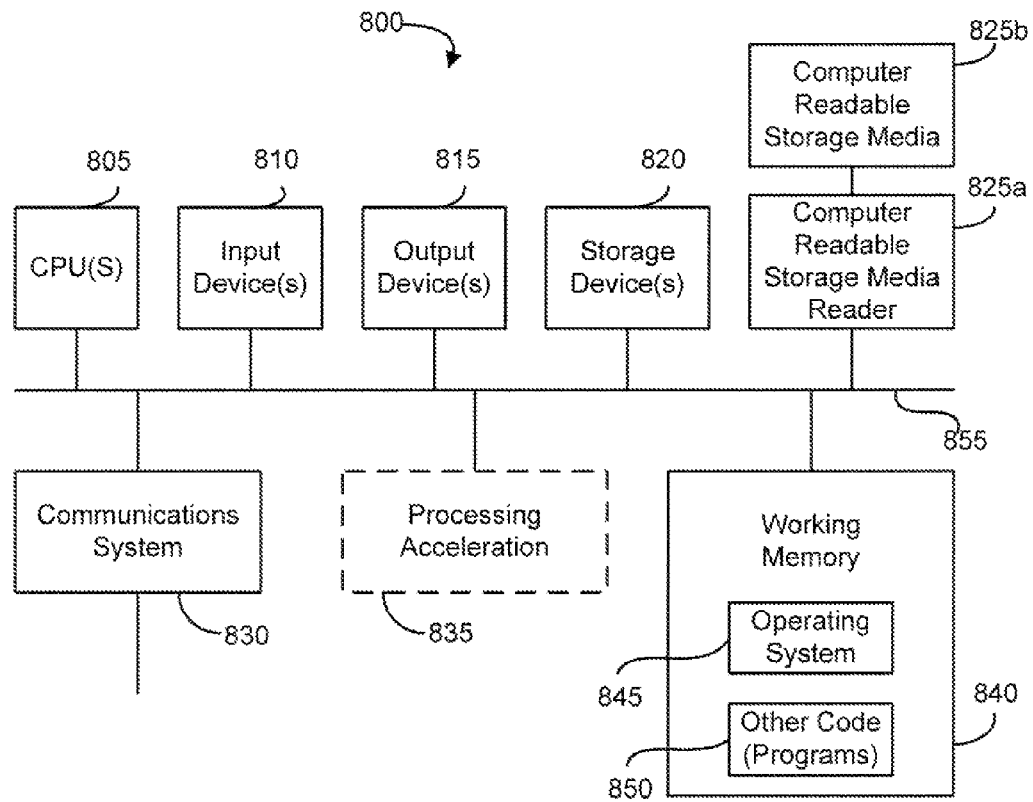
FIG. 8 is a block diagram illustrating an exemplary computer system in which embodiments of the present invention may be implemented.

FIG. 8 is a block diagram illustrating an exemplary computer system in which embodiments of the present invention may be implemented. As noted, a system in which the patch described herein may be implemented can include a reader, handheld device, and/or supporting system with any or all executing software for receiving, storing, and or manipulating temperature data from the sensing device of the patch. FIG. 8 illustrates one such exemplary computer system 800. The system 800 may be used to implement any of the supporting system, reader, handheld device, etc. described above. The computer system 800 is shown comprising hardware elements that may be electrically coupled via a bus 855. The hardware elements may include one or more central processing units (CPUs) 805, one or more input devices 810 (e.g., a mouse, a keyboard, etc.), and one or more output devices 815 (e.g., a display device, a printer, etc.). The computer system 800 may also include one or more storage device 820. By way of example, storage device(s) 820 may be disk drives, optical storage devices, solid-state storage device such as a random access memory ("RAM") and/or a read-only memory ("ROM"), which can be programmable, flash-updateable and/or the like.

The computer system 800 may additionally include a computer-readable storage media reader 825a, a communications system 830 (e.g., a modem, a network card (wireless or wired), an infra-red communication device, etc.), and working memory 840, which may include RAM and ROM devices as described above. In some embodiments, the computer system 800 may also include a processing acceleration unit 835, which can include a DSP, a special-purpose processor and/or the like.

The computer-readable storage media reader 825a can further be connected to a computer-readable storage medium 825b, together (and, optionally, in combination with storage device(s) 820) comprehensively representing remote, local, fixed, and/or removable storage devices plus storage media for temporarily and/or more permanently containing computer-readable information. The communications system 830 may permit data to be exchanged with the network 820 and/or any other computer described above with respect to the system 800.

The computer system 800 may also comprise software elements, shown as being currently located within a working memory 840, including an operating system 845 and/or other code 850, such as an application program (which may be a client application, web browser, mid-tier application, RDBMS, etc.). It should be appreciated that alternate embodiments of a computer system 800 may have numerous variations from that described above. For example, customized hardware might also be used and/or particular elements might be implemented in hardware, software (including portable software, such as applets), or both. Further, connection to other computing devices such as network input/output devices may be employed. Software of computer system 800 may include code 850 for implementing embodiments of the present invention as described herein.

As noted, software of the system 800 can receive, store, and/or manipulate temperature data from the sensing device of the vaginal ring. For example, the software can include algorithms that collect and possibly filter the individual temperature measurements to report an actual temperature and/or to establish a unique baseline for each individual. Additionally or alternatively, the software can alert of an increase from an individual baseline, for example to notify the user of a possible onset of ovulation.

Figure 9:
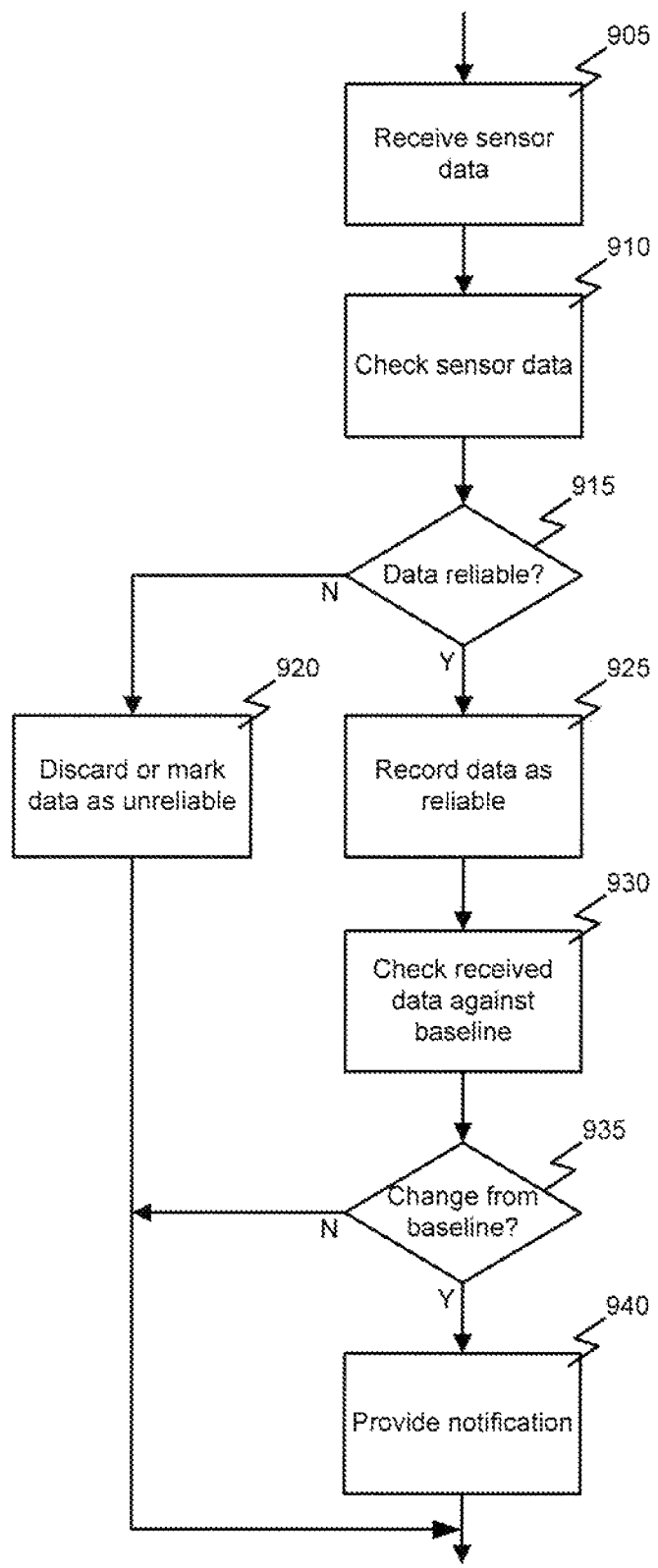
FIG. 9 is a flowchart illustrating an exemplary process for sensing using a sensor device according to one embodiment of the present invention.

FIG. 9 is a flowchart illustrating an exemplary process for remote sensing using a sensor device according to one embodiment of the present invention. In this example, processing begins with receiving 905 sensor data from one or more sensors of a sensing device as described above. The received sensor data can be checked 910 for reliability. For example, such checks can include but are not limited to various parity checks and/or determining whether the received data indicates the sensing device(s) reaching a steady or reliable state. Based on these checks, a determination 915 can be made as whether the data is acceptable or reliable. If the sensor data is determined 915 to not be acceptable, the data is considered to be unreliable, e.g., not yet stable or otherwise invalid, and can thus be discarded 920. Alternatively, rather than discarding the data, it may be recorded but not relied upon for other purposes, for example for comparison of current and past sensor data. If the sensor data is determined 915 to be reliable, the data can be recorded 925 and/or utilized for monitoring, control, or other purposes. For example, the collected data can be used to establish a baseline for a particular individual over time. Since an individual's body temperature varies through-out a daily cycle, the baseline could vary with the time of day based on previous measurements for that time of day.

Reliable data can also be checked 930 against an established baseline. Based on this check 930, a determination 935 can be made as to whether the data indicates a change from the baseline, e.g., an increase in core body temperature indicating possible ovulation. If 935 a change is detected, a notification can be provided 940 to the user of the sensing device. For example, the notification can comprise an audible and/or visual message on a personal computer, cell phone, smart phone, or other device used to read data from the sensing device as described above.

It is to be understood that even though numerous characteristics and advantages of various embodiments of the present invention have been set forth in the foregoing description, together with the details of the structure and function of various embodiments of the invention, this disclosure is illustrative only, and changes may be made in detail, especially in matters of structure and arrangement of parts within the principles of the present invention to the full extent indicated by the broad general meaning of the terms in which the appended claims are expressed. For example, the elastic vaginal ring 100 can have multiple radio frequency devices, such as the device 200, wherein one radio frequency device is active and another is passive while still maintaining substantially the same functionality without departing from the scope and spirit of the present invention. Another example can include using an elastic vaginal ring 100 that is further impregnated with chemicals to act physiologically on a patient using the elastic vaginal ring 100, or has multiple various sensors, while still maintaining substantially the same functionality without departing from the scope and spirit of the present invention. Another example can include using multiple readers to obtain information acquired via the elastic vaginal ring 100, such as a hand-held reader, multiple hand-held readers, non hand-held readers, just to name a few examples while still maintaining substantially the same functionality without departing from the scope and spirit of the present invention. Further, though elements and methods are described herein exemplifying a first and second object or element, for example, this language is used herein to simplify the description indicative of a plurality of objects or elements. Finally, although the preferred embodiments described herein are directed to temperature sensing active transmitting or passive RFID devices, it will be appreciated by those skilled in the art that the teachings of the present invention can be applied to other wireless devices and systems that can be accommodated in a vaginal device that is substantially and entirely within a vaginal vault 600, without departing from the spirit and scope of the present invention.

In the foregoing description, for the purposes of illustration, methods were described in a particular order. It should be appreciated that in alternate embodiments, the methods may be performed in a different order than that described. It should also be appreciated that the methods described above may be performed by hardware components or may be embodied in sequences of machine-executable instructions, which may be used to cause a machine, such as a general-purpose or special-purpose processor or logic circuits programmed with the instructions to perform the methods. These machine-executable instructions may be stored on one or more machine readable mediums, such as CD-ROMs or other type of optical disks, floppy diskettes, ROMs, RAMs, EPROMs, EEPROMs, magnetic or optical cards, flash memory, or other types of machine-readable mediums suitable for storing electronic instructions. Alternatively, the methods may be performed by a combination of hardware and software.

While illustrative and presently preferred embodiments of the invention have been described in detail herein, it is to be understood that the inventive concepts may be otherwise variously embodied and employed, and that the appended claims are intended to be construed to include such variations, except as limited by the prior art.

What is claimed is:

1. A method comprising:
   receiving sensor data in a flexible sensing device, said flexible sensing device comprising a flexible circuit arrangement having at least one temperature sensor, a microcontroller, a flexible antenna, and a wireless transmitter, said flexible circuit arrangement disposed within a flexible ring configured for insertion into a vaginal vault of a user;
   processing by said microcontroller received sensor data, in-situ;
   and in response to processing the received sensor data, providing a wireless notification from said flexible ring to an external receiver, wherein the notification is related to a state of ovulation of the user.

2. The method of claim 1 and further comprising the step of determining, based on said step of processing, whether said received sensor data indicates a change in temperature for the user.

3. The method of claim 1, wherein said flexible ring comprises a smoothly surfaced flexible ring for long term retention within said user, and wherein said step of receiving sensor data from said flexible sensing device comprises the step of utilizing a flexible circuit board curled inside of and encapsulated within said flexible ring.

4. The method of claim 3, wherein said step of receiving sensor data from said flexible sensing device further comprises the step of utilizing said flexible antenna and wherein said flexible antenna is curled in and encapsulated within said flexible ring.

5. The method of claim 4, wherein said step of utilizing a flexible antenna curled in and encapsulated within said flexible ring comprises the step of utilizing a multi turn loop flexible antenna that is curled in and encapsulated within said flexible ring.

6. The method of claim 5, wherein said step of receiving sensor data from said flexible sensing device comprising a flexible circuit arrangement having at least one temperature sensor, a microcontroller, and a wireless transmitter, comprises the step of utilizing a wireless transmitter selected from a group consisting of: a 308 MHz wireless transmitter, a 900 MHz wireless transmitter, a 915 MHz wireless transmitter, a 134.2 KHz wireless transmitter, a 13.56 MHz wireless transmitter, a 2.4 GHz wireless transmitter, and a 434 MHz wireless transmitter.

7. The method of claim 2, and further comprising the step of establishing a baseline temperature for said user.

8. The method of claim 7, wherein said step of determining whether the received data indicates a change from said baseline temperature for said user comprises the step of determining if the received sensor data indicates a rise in a core temperature of the user, and wherein said step of providing a notification comprises the step of providing a notification relative to ovulation of said user.

9. The method of claim 8, wherein said step of processing by said microcontroller the received sensor data comprises the step of in-situ processing said data within said flexible sensing device by said microcontroller in order to make a determination relative to said step of providing a notification from said flexible ring.

10. The method of claim 1, wherein said step of receiving sensor data from a flexible sensing device, the sensing device comprising a flexible circuit arrangement having at least one temperature sensor, a microcontroller, and a wireless transmitter comprises the step of receiving sensor data from a flexible sensing device, the sensing device comprising a flexible circuit arrangement having at least one temperature sensor, a microcontroller, and a secure wireless transmitter, and wherein said step of providing a notification from said flexible ring comprises the step of securely providing a notification from said flexible ring.

11. The method of claim 10, wherein said step of securely providing a notification from said flexible ring comprises the step of password encrypting a notification communication from said flexible ring.

12. The method of claim 9, and further comprising the step of logging sensor readings into said flexible sensing device for later use.

13. The method of claim 12, wherein said step of logging sensor readings into said flexible sensing device for later use comprises the step of logging time/date information for said sensor readings into said flexible sensing device.

14. The method of claim 7, wherein said step of establishing a baseline temperature for said user comprises the step of establishing a baseline temperature that varies with the time of day based on previous measurements for that time of day for said user.

15. The method of claim 2, wherein said step of processing by said microcontroller the received sensor data comprises the step of determining whether said received data indicates that a reliable state has been reached.

16. The method of claim 1, and further comprising the steps of:
externally sending a signal to said flexible sensing device; and
causing activity by said flexible sensing device as a result of said step of externally sending a signal to said flexible sensing device.

17. The method of claim 16, wherein said step of externally sending a signal to said flexible sensing causes the step of turning on or off said flexible sensing device.

18. The method of claim 1, and further comprising the step of externally powering said flexible sensing device.

19. A flexible wireless sensing device comprising:
a flexible circuit arrangement having:
at least one temperature sensor,
a flexible antenna,
a microcontroller,
and a wireless transmitter,
wherein said flexible circuit arrangement is disposed within a smooth flexible elastic ring and wherein the smooth flexible elastic ring is configured to be compressed into a spring-loaded state for self-insertion into a vaginal vault of a user, wherein said microcontroller is configured to process data, in situ, from said at least one temperature sensor during long term retention of the device within said vaginal vault of the user, and said wireless transmitter is configured to transmit externally of the user a password encrypted notification, based upon said processed data, which is indicative of a state of ovulation of the user.

* * * * *